United States Patent
Bohrmann et al.

(10) Patent No.: US 9,848,926 B2
(45) Date of Patent: Dec. 26, 2017

(54) SYSTEM FOR THE FIXATION OF BONE SEGMENTS OR BONE FRAGMENTS

(75) Inventors: Peter Bohrmann, Muehlheim (DE); Lorenz Gabele, Sauldorf (DE); Axel Waizenegger, Muehlheim (DE); Heiner Wild, Spaichingen (DE)

(73) Assignee: Karl Leibinger Medizintechnik GmbH, Muehlheim/Donau (DE)

( * ) Notice: Subject to any disclaimer, the term of this patent is extended or adjusted under 35 U.S.C. 154(b) by 1502 days.

(21) Appl. No.: 11/525,235

(22) Filed: Sep. 20, 2006

(65) Prior Publication Data

US 2007/0093837 A1    Apr. 26, 2007

(30) Foreign Application Priority Data

Sep. 20, 2005 (DE) .................... 20 2005 014 850 U

(51) Int. Cl.
*A61B 17/86* (2006.01)

(52) U.S. Cl.
CPC .............................. *A61B 17/8605* (2013.01)

(58) Field of Classification Search
USPC ....... 606/280, 308, 309, 315, 289, 307, 311, 606/319, 321; 411/411, 426, 308, 311, 411/339
See application file for complete search history.

(56) References Cited

U.S. PATENT DOCUMENTS

| | | | |
|---|---|---|---|
| 3,541,918 A * | 11/1970 | Johnson .................. | 411/412 |
| 5,470,334 A * | 11/1995 | Ross et al. .................. | 606/916 |
| 6,129,730 A * | 10/2000 | Bono et al. .................. | 606/291 |
| 6,306,136 B1 * | 10/2001 | Baccelli .................. | 606/279 |
| 2005/0131413 A1 * | 6/2005 | O'Driscoll et al. ............ | 606/73 |
| 2006/0149265 A1 * | 7/2006 | James et al. .................. | 606/73 |
| 2006/0200151 A1 * | 9/2006 | Ducharme et al. ............ | 606/73 |
| 2007/0009340 A1 * | 1/2007 | Van Cor ...................... | 411/426 |

* cited by examiner

*Primary Examiner* — David Bates
(74) *Attorney, Agent, or Firm* — McCoy Russell LLP

(57) ABSTRACT

The present disclosure relates to a system for the fixing of bone segments or bone fragments comprising an implant plate or an implant surface plate having a bore or a cut-out and comprising an implant screw which can be guided through the bore or cut-out of the plate, wherein the implant screw has a screw shaft and a screw head and wherein both the screw shaft and the screw head have a thread with identical pitches.

18 Claims, 1 Drawing Sheet

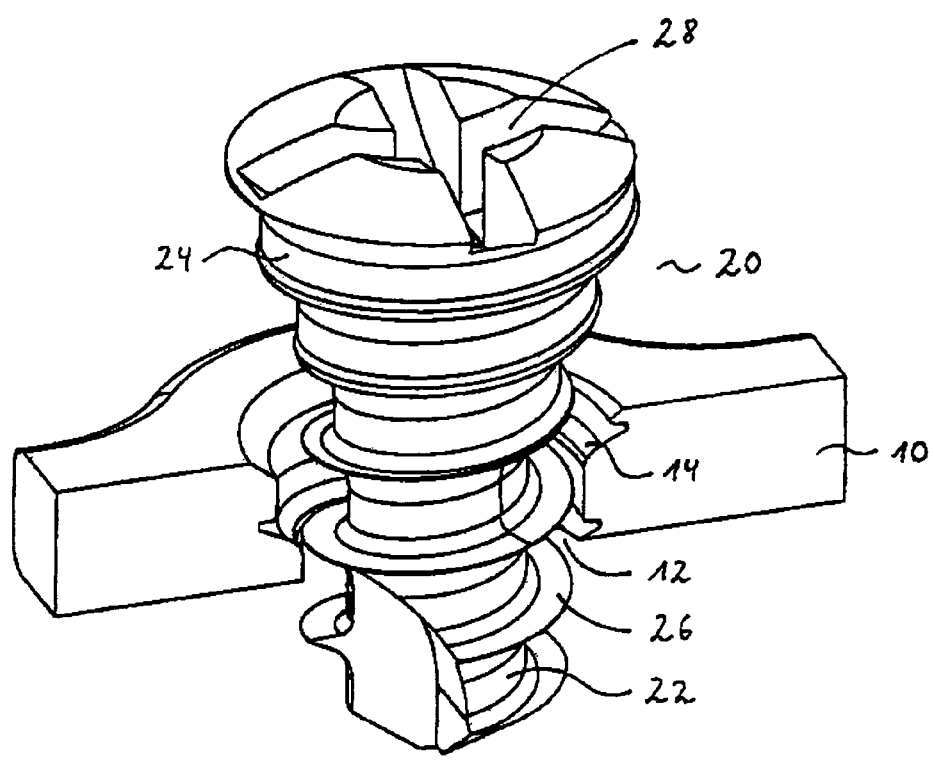

SYSTEM FOR THE FIXATION OF BONE SEGMENTS OR BONE FRAGMENTS

CROSS-REFERENCE TO RELATED APPLICATION

This application claims priority to German Utility Model Application Serial No. 20 2005 014 850.4 filed Sep. 20, 2005, which is hereby incorporated by reference in its entirety for all purposes.

FIELD

The present disclosure relates to a system for the fixation of bone segments or bone fragments.

BACKGROUND AND SUMMARY

Systems of this type are known in various embodiments in the area of medical engineering. Systems are known, for example, which have a screw as a fastening means which has a cylindrical screw head on which a thread is located which has a larger diameter than the screw shaft. The thread of the screw head is a metric thread of a fine pitch. The screw shaft which is introduced into the bone tissue is likewise provided with a thread which has a larger pitch in comparison with the thread of the screw head.

In systems with screws of this type, there is a disadvantage in that compression effects occur on the tightening of the screw which are due to the fact that a thread is provided in the head region of the screw with a smaller metric pitch than at the bone thread at the shaft of the screw.

It is the object of the present disclosure to further develop a system of the initially named type such that the disadvantages known from the prior art are avoided, in particular such that compression effects do not occur.

This object is solved by a system for the fixing of bone segments or bone fragments comprising an implant plate or an implant surface plate having a bore or a cut-out with an implant screw which is guided through a bore or cut-out of the implant plate or implant surface plate (mesh). The implant screw has a screw shaft and a screw head, with the screw shaft and the screw head having threads or threaded sections which are made with identical pitches.

A fast, simple and secure solution of fastening implant screws through an implant plate or an implant surface plate (mesh) to bones and of simultaneously establishing a locking connection between the screw and the plate is made available by the system in accordance with the present disclosure. It is thus possible in a simple manner to fix bone segments or bone fragments securely in their spatial relationship to other bone parts such that a later displacement does not take place and a fast, positionally secure healing can take place.

In a preferred embodiment of the present disclosure, two components of the system, that is the screw and the plate, form a unit which is contiguous in the installed state, but which is releasable per se. In the assembled state, both components, that is the implant screw and the plate, are locked or anchored to one another. This is achieved by a thread in accordance with the present disclosure which preferably extends from the screw shaft in an uninterrupted manner up to and into the screw head.

Due to the identical pitch of the thread in both regions, that is at the screw shaft and at the screw head, or over the total screw up to the head, the aforesaid compression effects do not occur which can occur in solutions known from the prior art.

It is particularly advantageous for the screw head to have a larger diameter than the screw shaft. If the head diameter of the screw is enlarged with respect to the screw shaft diameter, the screw can first be screwed through the plate into the bone without a connection to the place and only locks when the enlarged screw head in the plate is reached.

An aspect of the present disclosure is particularly preferred in which the screw shaft merges continuously, that is constantly, into the screw head. In a preferred aspect of the present disclosure, the thread extends continuously from the screw shaft up to and into the screw head.

The screw shaft can be cylindrical, for example.

Provision can furthermore be made for the screw head to be designed with a constantly increasing diameter starting from the screw shaft. The shape of the screw head can be any desired one per se. It is, for example, conceivable that the screw head is made conical or similar to a cone, similar to a sphere or in the form of a hemisphere or in the form of other shaped curves. It is generally conceivable to design the screw head with outer sides straight or curved in longitudinal section or also with convex or concave outer sides.

In a preferred aspect of the present disclosure, provision is made for it to be a single-start thread; but multi-start threads can also be realized.

The screw, in particular the screw head, can have a recess for a tool for the turning of the screw. It can, for example, be a recess which is made such that an inner or outer shape-matched connection is maintained with the tool. For example, a recess in the form of a slit, a crossed recess, an inner polygonal recess (e.g. a hexagonal or square recess), a star-shaped or torx-shaped recess are conceivable, as are all other known drive variants. Analogously, an outer shape-matched connection is also conceivable.

BRIEF DESCRIPTION OF THE FIGURE

Further details and advantages of the present disclosure will be explained in more detail with reference to an embodiment shown in the drawing.

The only drawing (FIG. 1) shows, in a schematic representation, an implant plate with an implant screw in accordance with the present disclosure received in the bore.

DETAILED DESCRIPTION

The system in accordance with the present disclosure comprises the implant plate or of the implant surface plate (mesh) 10 which has a bore 12 with an internal thread 14. The implant screw 20, which has a shaft 22 and a head 24, is introduced through the bore.

The thread 26 extends over the total length of the screw, that is both in the region of the screw shaft 22 and in the region of the screw head 24, such that the thread pitch is identical over the total length of the screw. An uninterrupted bone thread 26 is thus present up to and into the head 24 of the screw 20.

As can be seen from the drawing, the screw head 24 is made conical. Differently shaped curves of the thread in the screw head can naturally be realized, for example similar to a cone, similar to a sphere or also other shaped curves.

As can further be seen from the drawing, the diameter of the screw head 24 is enlarged with respect to the diameter of the screw shaft 22. The thread diameter thus also increases from the screw shaft 22 to the screw head 24. The advantage can thereby be achieved that the screw 20 can initially be screwed through the bore 12 of the plate 10 into the bone without any connection to the plate 10. A locking connection only takes place when the external thread of the enlarged screw head 24 comes into engagement with the internal thread 14 of the bore 12 of the plate 10. A locking connection is hereby achieved between the plate 10 and the screw 20.

The drive 28 is located on the upper side of the screw head 24 and is made in the embodiment shown as a crossed recess for the reception of a corresponding tool. Different drives, also drive possibilities by means of an external shape-matched connection, can naturally also be realized.

Compression effects which can occur when e.g. a screw has a smaller (metric) pitch in the head region than the bone thread at the shaft of the screw do not arise due to the identical pitch of the thread 26 over the total length of the screw 20 up to and into the region of the head 24. The screw in accordance with the present disclosure in accordance with the embodiment shown here is characterized in that an uninterrupted bone thread up to the head is present. A fast, simple and secure solution of fastening implant screws through an implant plate or an implant surface plate to bones and of simultaneously ensuring a locking connection between the screw and the plate is made available by the system in accordance with the present disclosure.

The invention claimed is:

1. A system for the fixing of bone segments or bone fragments comprising:
an implant plate or an implant surface plate having a bore or a cut-out; and
an implant screw which can be guided through the bore or cut-out of the plate, wherein the implant screw has a screw shaft and a screw head, wherein both the screw shaft and the screw head have a thread with identical pitches, wherein the screw head has a larger outer thread diameter than the screw shaft, wherein the bore or cut-out of the plate is provided with an internal thread and the thread of the screw head is able to engage the internal thread of the bore or cut-out of the plate, wherein an outer thread diameter of the screw shaft is less than an inner thread diameter of the bore or cut-out of the plate so that the implant screw is initially screwed through the bore or cut-out of the plate without any connection to the plate, and wherein a thread height in a region of the screw head is smaller than a thread height in a region of the screw shaft.

2. The system in accordance with claim 1, wherein the thread is made in an uninterrupted manner from the screw shaft up to the screw head.

3. The system in accordance with claim 1, wherein the screw shaft merges continuously into the screw head.

4. The system in accordance with claim 1, wherein the screw shaft is cylindrical.

5. The system in accordance with claim 1, wherein the screw head is made with an outer thread diameter increasing constantly starting from the screw shaft.

6. The system in accordance with claim 1, wherein the screw head has straight or curved outer sides in longitudinal section.

7. The system in accordance with claim 1, wherein the screw head is conical, hemispherical, concave or convex.

8. The system in accordance with claim 1, wherein the thread is made with a single start.

9. The system in accordance with claim 1, wherein the screw has a recess for a tool to turn the screw.

10. The system in accordance with claim 9, wherein a mount is made such that an internal or external shape-matched connection can be achieved with the tool.

11. The system in accordance with claim 1, wherein the thread is made with a multi-start.

12. The system in accordance with claim 1, wherein the thread of the screw head and the internal thread of the bore or cut-out are engaged in a locking connection in an installed state, wherein the locking connection is releasable.

13. The system in accordance with claim 1, wherein the screw only locks to the plate via the screw head.

14. A bone fixation system for the fixing of bone segments or bone fragments comprising:
an implant plate or an implant surface plate having a bore or a cut-out; and
a bone implant screw which can be guided through the bore or cut-out of the plate, wherein the bone implant screw has a screw shaft and a screw head, wherein both the screw shaft and the screw head have a thread with identical pitches, wherein the screw head has a larger outer thread diameter than the screw shaft, wherein the bore or cut-out of the plate is provided with an internal thread and the thread of the screw head is able to engage the internal thread of the bore or cut-out of the plate, wherein an outer thread diameter of the screw shaft is less than an inner thread diameter of the bore or cut-out of the plate so that the implant screw is initially screwed through the bore or cut-out of the plate without any connection to the plate, and wherein a thread height in a region of the screw head is smaller than a thread height in a region of the screw shaft.

15. The system in accordance with claim 14, wherein the thread is made in an uninterrupted manner from the screw shaft up to the screw head, the screw shaft merges continuously into the screw head, and the screw shaft is cylindrical.

16. The system in accordance with claim 15, wherein the screw head is made with an outer thread diameter increasing constantly starting from the screw shaft.

17. The system in accordance with claim 16, wherein the screw head has straight or curved outer sides in longitudinal section.

18. The system in accordance with claim 16, wherein the screw head is conical, hemispherical, concave or convex, and wherein a mount is made such that an internal or external shape-matched connection can be achieved with a tool.

* * * * *